US008747755B2

(12) United States Patent
Larsson

(10) Patent No.: US 8,747,755 B2
(45) Date of Patent: Jun. 10, 2014

(54) COMBINED ELECTRONIC DISPENSER AND AIR FRESHENER

(75) Inventor: Bjorn Larsson, Billdal (SE)

(73) Assignee: SCA Hygiene Products AB, Gothenburg (SE)

( * ) Notice: Subject to any disclaimer, the term of this patent is extended or adjusted under 35 U.S.C. 154(b) by 807 days.

(21) Appl. No.: 12/516,668

(22) PCT Filed: Dec. 1, 2006

(86) PCT No.: PCT/SE2006/001379
§ 371 (c)(1),
(2), (4) Date: May 28, 2009

(87) PCT Pub. No.: WO2008/066426
PCT Pub. Date: Jun. 5, 2008

(65) Prior Publication Data
US 2010/0068092 A1 Mar. 18, 2010

(51) Int. Cl.
*A61L 9/00* (2006.01)
*A61L 9/14* (2006.01)
*A47K 10/38* (2006.01)

(52) U.S. Cl.
CPC .. *A61L 9/14* (2013.01); *A47K 10/38* (2013.01)
USPC .......................................... 422/123; 422/107

(58) Field of Classification Search
CPC .................................. A61L 9/14; A47K 10/38

USPC ................ 422/5, 28, 106, 107, 120, 123, 124
See application file for complete search history.

(56) References Cited

U.S. PATENT DOCUMENTS

| 2,539,059 A | 1/1951 | Cohn |
| 3,192,008 A | 6/1965 | Dwyer |
| 5,312,021 A | 5/1994 | Nelson |
| 6,000,658 A | 12/1999 | McCall |
| 6,883,787 B2 * | 4/2005 | Allen ............................ 422/124 |
| 2003/0168549 A1 | 9/2003 | Formon |
| 2004/0223943 A1 | 11/2004 | Woo |

FOREIGN PATENT DOCUMENTS

| AU | 725813 | 10/2000 |
| EP | 1610901 | 1/2006 |
| GB | 618311 | 2/1949 |
| WO | 9731718 | 5/2001 |
| WO | 2004089552 | 1/2006 |

OTHER PUBLICATIONS

International Search Report dated Jun. 15, 2007, in PCT application.

* cited by examiner

*Primary Examiner* — Timothy Cleveland
(74) *Attorney, Agent, or Firm* — Buchanan Ingersoll & Rooney PC

(57) ABSTRACT

A system includes an electronic dispenser for web material and an air freshener device. Activation of the web dispensing mechanism a predetermined number of times activates the air freshener mechanism at least once. A method for deodorizing a space using the system is also disclosed.

14 Claims, 2 Drawing Sheets

COMBINED ELECTRONIC DISPENSER AND AIR FRESHENER

TECHNICAL FIELD

The present invention relates to a system and a method for removing malodour in the surroundings. The system and method are correlated with the frequency in which the surroundings are used, and provide a rapid response to changes in this frequency.

BACKGROUND OF THE INVENTION

It is desirable for certain environments such as kitchens, bathrooms, toilets etc. to be deodorised. Air fresheners for concealing or removing undesirable odours are well-known, and are commercially available. Air fresheners often require the intervention of a user (e.g. pressing a button or spraying a canister of deodorant), which can prove unreliable and often present hygiene problems.

To provide a reliable source of deodorant, air fresheners are often set up to emit deodorant according to a predetermined schedule (e.g. using one or more logic circuits incorporating a timer). Timed air fresheners such as these can be adapted to release less deodorant at certain times (at night, for example). However, such systems are not strongly correlated with the frequency in which the environment is used, and cannot adapt quickly to situations where more or less deodorisation may be required. For example, public toilets in entertainment venues require more deodorisation during a pause in the performance or event than during the performance or event itself.

Air freshening systems are known which dispense deodorant in response to an indirect action by a user. These actions are usually mechanical, such as opening a door, lifting a toilet cover or opening a lid of a waste-bin. For example, U.S. Pat. No. 4,625,342 describes an air freshener which is actuated by the movement of a toilet flushing mechanism. An actuator arm in the toilet closes a switch to send an electrical signal to the air freshener. However, none of these systems display the flexibility of the present invention.

US 2004/0223943 describes air fresheners that may comprise a container with a propellant for spraying the contents. Various deodorant compositions and features of the air fresheners are described.

WO 97/31718 discloses an electrostatic spraying device which is solar driven to avoid changing batteries. Several operation modes are described: spraying when the batteries are fully-charged and spraying upon demand when a switch is activated. The switch can be activated manually (e.g. press button), electronically (e.g. field effect transistor) or optically (e.g. interruption of a light beam).

US 2003/0168549 provides an example of an electric dispenser for web material. Many aspects of the dispensing can be controlled by means of an electronic control system, a clock system and several internal sensors for paper position, motor consumption and clock circuits.

U.S. Pat. No. 6,883,787 describes a paper towel dispenser with deodorizer. The drive used to rotate the paper towel is used to drive a fan which passes air through the paper towel roll core and out through a hole in the housing. The roll core contains deodorising material.

There remains a need for an air freshener system which is linked to the frequency in which the environment is used, which can assess situations where more or less deodorisation is required and respond quickly, providing more or less deodorant. It would be advantageous if the air freshener system were powered in a simple fashion, and functioned in a simple way (e.g. without requiring complicated sensors and logic circuits in the air freshener). It would also be advantageous if the air freshener system were integrated with other devices in the same surroundings.

SUMMARY OF THE INVENTION

In a first aspect, the present invention provides an improved system for deodorising a space.

The system comprises an electronic dispenser for web material and at least one air freshener. The electronic dispenser comprises a web dispensing mechanism and electronic means for activation of the web dispensing mechanism. The at least one air freshener comprises an air freshener mechanism and electronic means for activation of the air freshener mechanism. The means for activation of the air freshener mechanism is linked to the means for activation of the web dispensing mechanism, such that activation of the web dispensing mechanism a predetermined number of times activates the air freshener mechanism at least once.

After users have washed their hands, e.g. after a toilet visit or after preparing food, they need to dry them. They therefore activate the dispenser of web material, which in turn activates the air freshener. In this way, the frequency in which an environment such as a washroom is used (which is linked to the activity of a dispenser of web material) can in turn be linked to the activity of the air freshener.

Suitably, a control unit is located between the means for activation of the web dispensing mechanism and the means for activation of the air freshener mechanism. The control unit links the means for activation of the air freshener mechanism to the means for activation of the web dispensing mechanism, such that activation of the web dispensing mechanism a predetermined number of times activates the air freshener mechanism at least once.

The control unit may be arranged such that the web dispensing mechanism must be activated more than once; e.g. twice, three times, four times or five times in order to activate the air freshener mechanism at least once. Preferably, the control unit can be adjusted to activate the air freshener mechanism more than once for a single activation of the web dispensing mechanism, or to activate the air freshener mechanism only after the web dispensing mechanism has been activated more than once.

The air freshener may comprise a container containing deodorising fluid. The container may additionally contain an antibacterial substance and/or an anti-allergenic substance. The air freshener mechanism is suitably arranged to spray deodorant into the atmosphere surrounding the air freshener, said deodorant being in the form of droplets, particles or gas. One way in which this might be achieved is that the air freshener mechanism comprises an aerosol head. Alternatively, the air freshener mechanism comprises a pair of capillaries across which an electric spark is applied to vaporize a portion of the contents of the air freshener.

The air freshener mechanism may be electrically-powered from the same power source as the electric dispenser, such as by e.g. one or more batteries, solar panels or the mains electricity supply.

It is useful if the air freshener comprises means to determine the amount of deodorising fluid that is to be dispensed from said air freshener in a predetermined time period. The air freshener may also comprise means to increase or decrease the amount of deodorising fluid that is to be dispensed from said air freshener in a single activation of the air freshener mechanism.

The means for activation of the web dispensing mechanism can be selected from the group comprising a capacitive sensor, a light sensor, an infra-red sensor, a push-button and a lever. As an alternative, the means for activation of the web dispensing mechanism comprises means arranged within the web dispensing mechanism which detects tension applied to the leading edge of the web material by the user and activates the web dispensing mechanism.

In a second aspect, the present invention provides a method for deodorising a space. The method comprises: providing a system according to the invention in said space and activating the web dispensing mechanism a predetermined number of times, thereby also activating the air freshener mechanism at least once and deodorising said space.

The air freshener mechanism may be activated each time the web dispensing mechanism is activated. However, in certain circumstances, the air freshener mechanism is only activated after the web dispensing mechanism has been activated more than once; e.g. twice, three times, four times or five times.

Definitions

A deodorant is a chemical substance or a mixture of more than one chemical substance which is used to treat malodour. Deodorants may themselves be sufficiently aromatic and persistent in the surroundings that malodours are concealed under the smell of the deodorant. Some deodorants may also react chemically or physically with the malodour, removing it from the surroundings. Deodorants may be liquid or gaseous. In the context of the present invention, the term "deodorant" includes terms such as perfumes, scents and aromas. Common deodorants for use in air fresheners are often small organic molecules which include at least one ester, ketone or aldehyde moiety. Suitable deodorants for use in the present invention are listed in US patent application no. 2004/0223943.

In the present context, the term "electronic" when used in reference to a component is used to mean that the component is powered by electricity and requires logic circuits to control the component. In its simplest form, the logic circuit responds to the presence or absence of an input signal and provides an appropriate output signal. Standard logic circuits which can be used in the present invention for controlling a component are described in e.g. US patent application no. 2003/0168549.

DETAILED DESCRIPTION OF PREFERRED EMBODIMENTS

Figure 1:
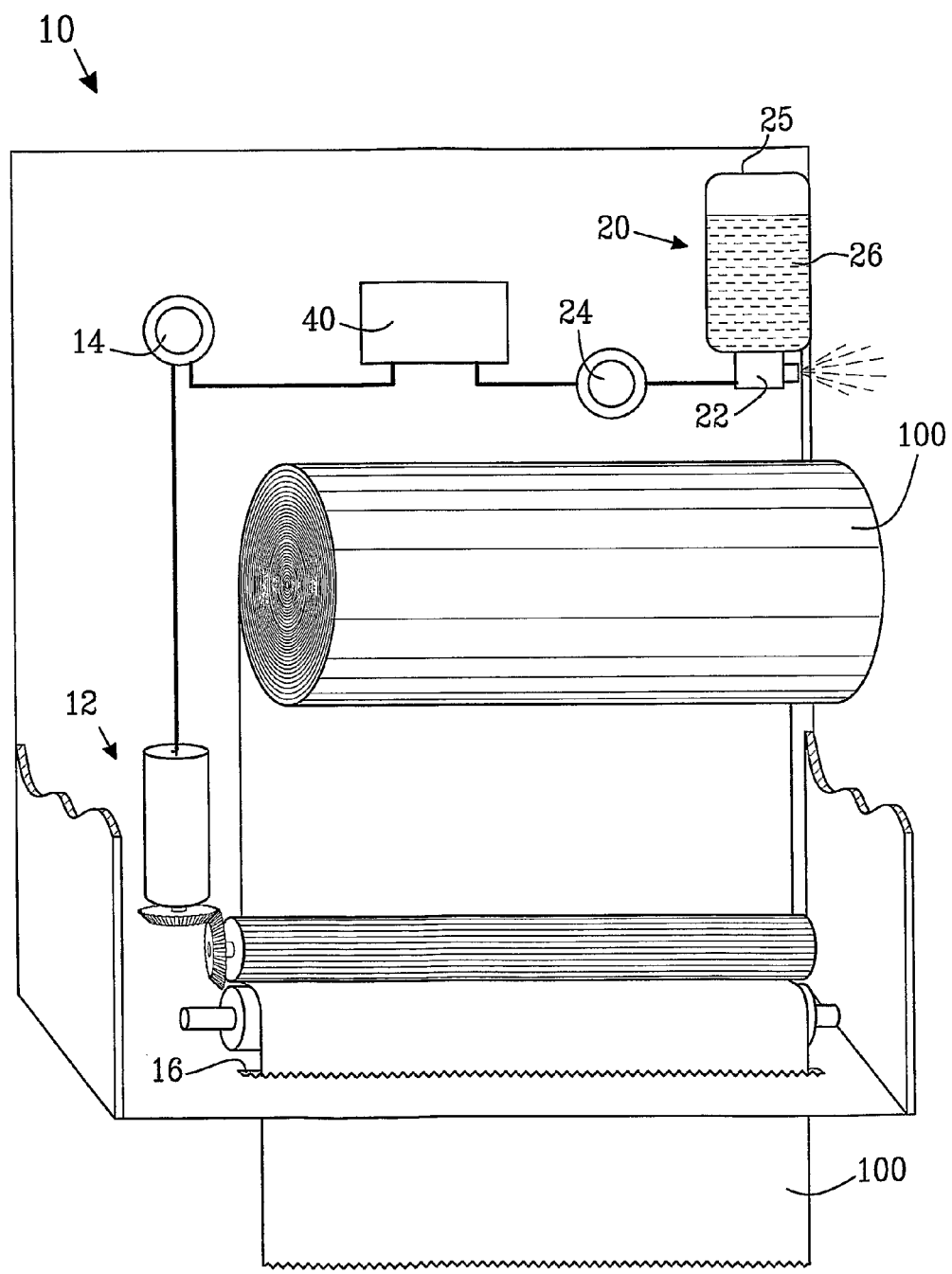
FIG. 1 illustrates the system according to the invention.

The combined dispenser and air freshener system is shown in a general form in FIG. 1.

The system comprises an electronic dispenser 10 for web material 100. The web material 100 is mounted or suspended within the dispenser 10 and is arranged such that the leading edge of the web material 100 can be fed from the dispenser 10 through a dispensing opening 16. The embodiment shown in FIG. 1 is designed to hang on a wall or other vertical surface such that the leading edge of the web material 100 is dispensed via the dispensing opening 16 which is located on the underside of the dispenser 10.

The web material 100 may be in the form of a roll. FIG. 1 illustrates a peripheral-feed roll. The web material 100 may also be in the form of a stack of sheets, which may be interfolded or interleaved such that dispensing of a first sheet causes the next sheet to follow. Whether in the form of rolls or stacks of sheets, the web material 100 may comprise perforation lines or other weakened regions so that dispensing of a single length of web material is simplified.

The web material 100 for use in the present invention may be any type of web material which can be dispensed from the type of dispenser 10 which is illustrated in FIG. 1 and described herein. Preferably, the web material 100 is tissue paper. Alternatively, the web material 100 may be nonwoven material.

The electronic dispenser 10 comprises a web dispensing mechanism 12. Upon activation, the web dispensing mechanism 12 acts to feed web material 100 through the dispensing opening 16 of the dispenser 10 to the user. The web dispensing mechanism 12 may comprise one or more rollers, one or more drive motors, one or more cutting or tearing mechanisms, one or more braking mechanisms, and mechanisms which link these components of the web dispensing mechanism 12 so that they operate in unison (e.g. cog wheels, linking arms, levers etc.). A simple arrangement of a motor and two rollers is shown in the embodiment of FIG. 1, although the skilled person will understand that more complex systems are possible.

Figure 2:
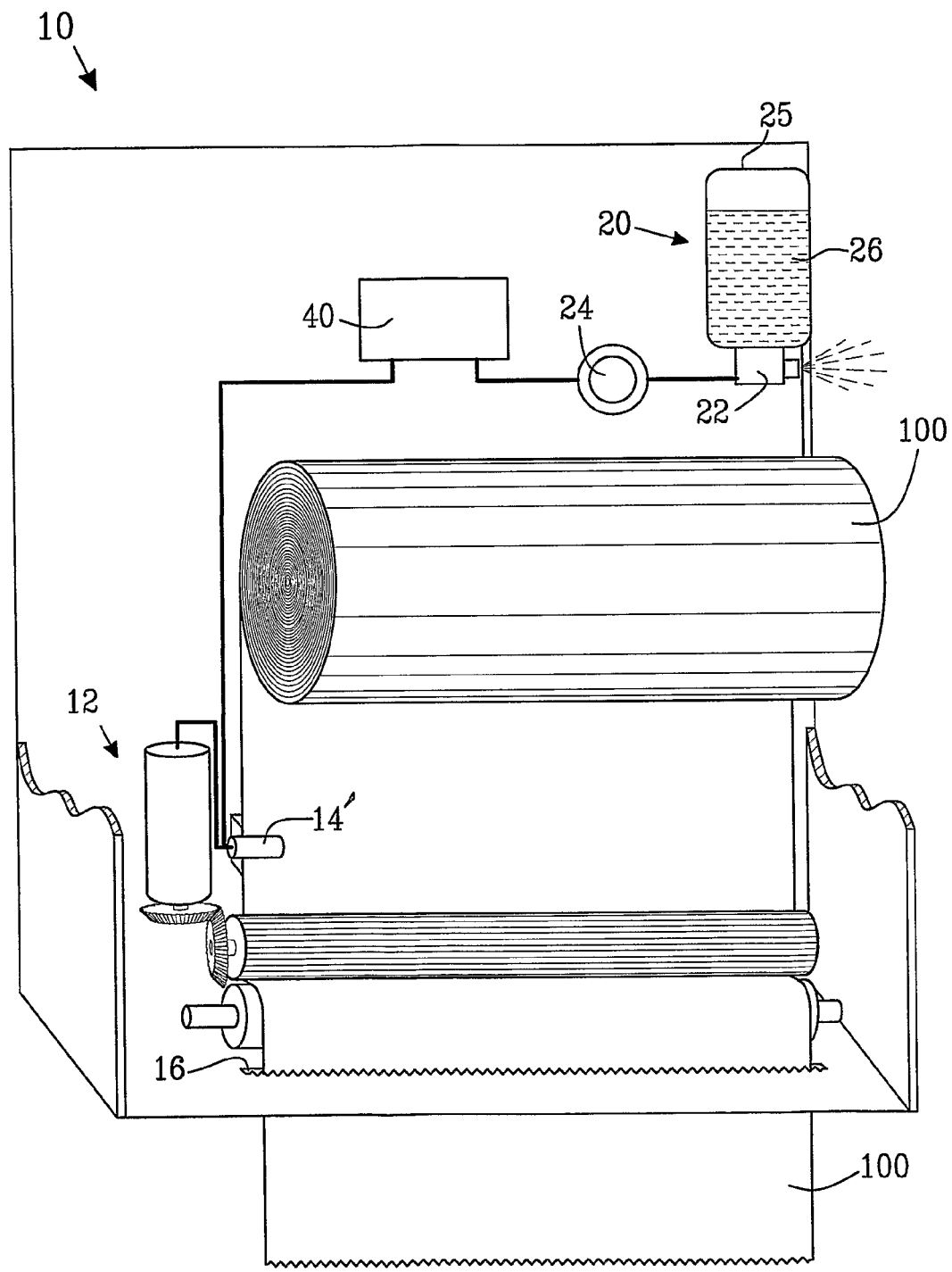
FIG. 2 illustrates an embodiment of the system.

The electronic dispenser 10 also comprises electronic means 14 for activation of the web dispensing mechanism 12. Upon receiving an input from a user, the electronic means 14 for activation of the web dispensing mechanism 12 provides a signal to the web dispensing mechanism 12, which operates, and in turn causes web material 100 to be dispensed. The means for activation 14 of the web dispensing mechanism 12 by a user may be selected from the group comprising a capacitive sensor, a light sensor, an infra-red sensor, a push-button and a lever. Alternatively, the means for activation 14 of the web dispensing mechanism 12 by a user comprises means 14' arranged within the web dispensing mechanism 12 which detects tension applied to the leading edge of the web material 100 by the user and activates the web dispensing mechanism 12 (see FIG. 2).

Therefore, the user pulling the leading edge of the web material 100 causes web material 100 to be dispensed. All of the above components may be used to detect the presence of a user or receive a signal from a user that web material 100 is required and to provide the appropriate signal to the web dispensing mechanism 12.

The system according to the invention comprises at least one air freshener device 20. Suitably, as shown in FIG. 1, the system comprises one air freshener device 20. Again, as shown in FIG. 1, the air freshener 20 may be in the same housing as the dispenser 10. This provides a convenient single unit which simplifies service and repair, as it is mounted within reach of the average user. However, it is also possible that the air freshener 20 is not in the same housing as the dispenser 10. For example, in public toilet facilities, the dispenser 10 may be mounted near the washbasins, while the air freshener 20 is mounted near the toilet. This also provides advantages, as the air freshener 20 can be located close to the source of malodour, and may be for instance mounted high on a wall so that the air freshening effect is maximised. One air freshener 20 may be mounted in each toilet cubicle and linked to the dispenser 10.

Typically, in the system according to the invention, the air freshener 20 comprises a container 25 containing deodorising fluid 26, as shown in FIG. 1. The container 25 may be for example a bottle of e.g. plastic or glass or metal containing the deodorant in liquid form. The container 25 may be pressurised, or contain a propellant, so that the deodorant is expelled more easily into the environment. The container 25 may additionally contain an antibacterial substance and/or an anti-allergenic substance, which is dispensed simultaneously with the deodorant and can provide improved hygiene or reduced allergies.

The air freshener device 20 comprises an air freshener mechanism 22. Upon activation, the air freshener mechanism 22 acts to expel deodorant from the air freshener and into the surrounding environment. More specifically, the air freshener mechanism 22 is arranged to spray deodorant into the atmosphere surrounding the air freshener 20, said deodorant being in the form of droplets, particles or gas. The air freshener mechanism 22 may comprise one or more pipes, filters or valves connected together to supply deodorant from the container 25 to the surrounding environment. In one particular embodiment, the air freshener mechanism 22 comprises an aerosol head. Other devices includes, but are not limited to nebulisers, foggers and spinning disk sprayers. Alternatively, the air freshener mechanism 22 comprises a pair of capillaries across which an electric spark is applied to vaporize the contents of the air freshener 20. Such air freshener mechanisms are described in e.g. EP1 610 901.

The air freshener device 20 may comprise means to determine the amount of deodorising fluid 26 that is to be dispensed from said air freshener 20 in a predetermined time period. This can be carried out by various indicators or sensors located inside or outside the container 25, or even through a simple window arrangement which allows the contents of the container 25 to be seen through the container wall. The amount of deodorising fluid 26 remaining in the container 25 can thus be readily determined.

The air freshener 20 may also comprise means to increase or decrease the amount of deodorising fluid 26 that has been dispensed from said air freshener 20 in a single activation of the air freshener mechanism 22. This allows the system to be adjusted to the surroundings (e.g. the size, the temperature or air currents in the room in which it is located).

Preferably, the air freshener mechanism 22 is electrically-powered from the same power source as the electric dispenser 10, such as e.g. one or more batteries, solar panels or the mains electricity supply.

The air freshener device 20 also comprises electronic means 24 for activation of the air freshener mechanism 22. Upon receiving an input, the electronic means 24 for activation of the air freshener mechanism 22 provides a signal to the air freshener mechanism 22, which operates, and in turn causes deodorant to be dispensed.

The means 24 for activation of the air freshener mechanism 22 is linked to the means 14 for activation of the web dispensing mechanism 12, such that activation of the web dispensing mechanism 12 a predetermined number of times activates the air freshener mechanism 22 at least once.

The linking between the means 24 for activation of the air freshener mechanism 22 and the means 14 for activation of the web dispensing mechanism 12 may be direct, in which case, the means 24 for activation of the air freshener mechanism is linked so that a signal is sent directly from the means for activation 14 of the web dispensing mechanism to the means 24 for activation of the air freshener mechanism 22.

The means 24 for activation of the air freshener mechanism 22 may also be linked indirectly to the means 14 for activation of the web dispensing mechanism 12. In this case, the input signal to the means 24 for activation of the air freshener mechanism 22 may be provided by the web dispensing mechanism 12, by a control unit 40 or by sensors which detect movement of the web material 100 itself.

Thus, a user desiring web material activates the web dispensing mechanism 12 (via the electronic means 14. Web material is then dispensed from the dispenser via the web dispensing mechanism 12. Once the web dispensing mechanism 12 has been activated the predetermined number of times, the air freshener mechanism 22 is activated at least once, hence deodorising the surrounding environment. This provides an effective and convenient way to deodorise an environment without additional action by the user.

The system according to the invention can allow that the air freshener mechanism 22 is activated once for each activation of the web dispensing mechanism 12 (i.e. when the predetermined number of times=1). However, the flexibility in the system allows variations in the number of times the air freshener mechanism 22 is activated for each activation of the web dispensing mechanism 12. For example, the system may be arranged such that the web dispensing mechanism 12 must be activated more than once; e.g. twice, three times, four times or five times in order to activate the air freshener mechanism 22 at least once. This means that, in busy periods when the dispenser is being used frequently, deodorant can be saved by not activating the air freshener mechanism 22 each time web material 100 is dispensed. For example, during busy periods, it may be sufficient that the air freshener mechanism 22 is activated only once per five activations of the web dispenser mechanism 12.

Furthermore, the system according to the invention can be arranged so as to measure the activity of the web dispensing mechanism 12 (which corresponds to the activity of the premises in which the system is installed) in a certain time period. The activity of the web dispensing mechanism 12 can then be used to determine the most appropriate activity for the air freshener mechanism 22. The air freshener mechanism 22 can then be activated accordingly. The correlation between activation of the web dispensing mechanism 12 and the air freshener mechanism 22 may be non-linear (e.g. logarithmic). For example, if the web dispensing mechanism 12 is activated twice per hour, the air freshener mechanism 22 may be activated only once per hour. If the web dispensing mechanism 12 is activated thirty times per hour, it may be sufficient that the air freshener mechanism 22 is activated ten times per hour. At busy periods, e.g. if the web dispensing mechanism 12 is activated a hundred times per hour, it may be sufficient that the air freshener mechanism 22 is activated only thirty times per hour. This flexibility in the system allows significant saving of deodorant, as the air freshener device 20 can respond in a general fashion to the web dispensing mechanism 12, but not necessarily upon each activation. It can also provide an extended deodorising effect in the surroundings, as the deodorising effect of a first spray of deodorant will be reinforced by the second (and further) sprays of deodorant. This system can also avoid that the level of deodorant in the surroundings becomes too high, as excessive deodorant causes wastage, can provoke allergic reactions and can also be perceived as malodour in high concentrations.

A control unit 40 may be located between the means 14 for activation of the web dispensing mechanism 12 and the means 24 for activation of the air freshener mechanism 22. The control unit 40 links the means 24 for activation of the air freshener mechanism to the means for activation 14 of the web dispensing mechanism 12, such that activation of the web dispensing mechanism 12 a predetermined number of times activates the air freshener mechanism 22 at least once. This allows the above-described functions to be carried out.

In one particular embodiment, the control unit 40 can be adjusted to activate the air freshener mechanism 22 more than once for a single activation of the web dispensing mechanism 12, or to activate the air freshener mechanism 22 only after the web dispensing mechanism 12 has been activated more than once. Such adjustment can be carried out manually, or the control unit 40 may comprise a feedback-loop which detects the activity of the web dispensing mechanism 12 and calculates the most suitable activation pattern for the air freshener mechanism 22 accordingly.

The present invention also provides a method for deodorising a space, said method comprising providing a system as described above in said space and activating the web dispensing mechanism 12 a predetermined number of times, thereby also activating the air freshener mechanism 22 at least once and deodorising said space. According to this method, the air freshener mechanism 22 may be activated each time the web dispensing mechanism 12 is activated. Furthermore, the air freshener mechanism 22 may only be activated after the web dispensing mechanism 12 has been activated more than once; e.g. twice, three times, four times or five times. A delay may be present in the system, such that the air freshener mechanism 22 is first activated at a certain predetermined time after the web dispensing mechanism 12 is first activated, such as e.g. 30 seconds after, 1 minute after, 2 minutes after, 5 minutes after the web dispensing mechanism 12 is first activated.

As above, the method according to the invention can include the step of measuring the activity of the web dispensing mechanism 12 (which corresponds to the activity of the premises in which the system is installed) in a certain time period. The activity of the web dispensing mechanism 12 can then be used to determine the most appropriate activity for the air freshener mechanism 22, and activating the air freshener mechanism 12 accordingly. The correlation between activation of the web dispensing mechanism 12 and the air freshener mechanism 22 may be non-linear (e.g. logarithmic). For example, if the web dispensing mechanism 12 is activated twice per hour, the air freshener mechanism 22 may be activated only once per hour. If the web dispensing mechanism 12 is activated thirty times per hour, it may be sufficient that the air freshener mechanism 22 is activated ten times per hour. At busy periods, e.g. if the web dispensing mechanism 12 is activated a hundred times per hour, it may be sufficient that the air freshener mechanism 22 is activated only thirty times per hour. This flexibility in the method allows significant saving of deodorant, as the air freshener device 20 can respond in a general fashion to the web dispensing mechanism 12, but not necessarily upon each activation. It can also provide an extended deodorising effect in the surroundings, as the deodorising effect of a first spray of deodorant will be reinforced by the second (and further) sprays of deodorant. This method can also avoid that the level of deodorant in the surroundings becomes too high, as excessive deodorant causes wastage, can provoke allergic reactions and can also be perceived as malodour in high concentrations.

The present invention should not be considered as limited by the above description and the enclosed Figures. In particular, the invention should not be considered as limited to the web dispensing mechanisms and the air freshener mechanisms which are described above. Rather, the scope of the invention should be determined by the appended claims.

The invention claimed is:

1. A system comprising:
an electronic dispenser for web material and
at least one air freshener device;
said electronic dispenser comprising a web dispensing mechanism and first electronic means for activation of said web dispensing mechanism, the at least one air freshener device being separate from the web dispensing mechanism;
said at least one air freshener device comprising an air freshener mechanism and second electronic means for activation of the air freshener mechanism; wherein
the second electronic means for activation of the air freshener mechanism is linked to the first electronic means for activation of the web dispensing mechanism, so that a signal is sent from the first electronic means for activation to the second electronic means for activation, such that activation of the web dispensing mechanism a predetermined two or more times activates the air freshener mechanism once.

2. The system according to claim 1, further comprising a control unit located between the first electronic means for activation of the web dispensing mechanism and the second electronic means for activation of the air freshener mechanism, said control unit linking the second electronic means to the first electronic means, such that activation of the web dispensing mechanism the predetermined two or more times activates the air freshener mechanism once.

3. The system according to claim 2, wherein the control unit can be adjusted to activate the air freshener mechanism only after the web dispensing mechanism has been activated.

4. The system according to claim 1, wherein the air freshener device comprises a container containing deodorizing fluid.

5. The system according to claim 4, wherein the container additionally contains an antibacterial substance and/or an anti-allergenic substance.

6. The system according to claim 1, wherein the air freshener mechanism is arranged to spray deodorant into the atmosphere surrounding the air freshener device, said deodorant being in the form of droplets, particles or gas.

7. The system according to claim 1, wherein the air freshener mechanism comprises an aerosol head.

8. The system according to claim 1, wherein the air freshener mechanism comprises a pair of capillaries across which an electric spark is applied to vaporize the contents of the air freshener device.

9. The system according to claim 1, wherein the air freshener mechanism is electrically-powered from the same power source as the electric dispenser.

10. The system according to claim 4, wherein the air freshener device comprises means to determine the amount of deodorizing fluid that has been dispensed from said air freshener device in a predetermined time period.

11. The system according to claim 4, wherein the air freshener device comprises means to increase or decrease the amount of deodorizing fluid that is to be dispensed from said air freshener device in a single activation of the air freshener mechanism.

12. The system according to claim 1, wherein the first electronic means for activation of the web dispensing mechanism by a user is selected from the group consisting of a camera, a capacitive sensor, a light sensor, an infra-red sensor and a push-button.

13. The system according to claim 1, wherein the first electronic means for activation of the web dispensing mechanism by a user comprises means arranged within the web dispensing mechanism which detects tension applied to the leading edge of the web material by the user and activates the web dispensing mechanism.

14. A system comprising:
an electronic dispenser for web material and
at least one air freshener device;
said electronic dispenser comprising a web dispensing mechanism and first electronic activator of said web dispensing mechanism, the at least one air freshener device being separate from the web dispensing mechanism;

said at least one air freshener device comprising an air freshener mechanism and second electronic activator of the air freshener mechanism; wherein the second electronic activator of the air freshener mechanism is linked to the first electronic activator of the web dispensing mechanism, so that a signal is sent from the first electronic activator to the second electronic activator, such that activation of the web dispensing mechanism a predetermined two or more times activates the air freshener mechanism once.

* * * * *